United States Patent [19]

Tsushima et al.

[11] Patent Number: 5,607,963
[45] Date of Patent: Mar. 4, 1997

[54] MALEIMIDE PESTICIDES AND COMPOSITIONS THEREOF

[75] Inventors: Kazunori Tsushima, Sanda; Takashi Furukawa; Tomonori Iwasaki, both of Takarazuka; Takao Ishiwatari; Mikako Nakamachi, both of Minoo, all of Japan

[73] Assignee: Sumitomo Chemical Company, Limited, Osaka, Japan

[21] Appl. No.: 456,309

[22] Filed: Jun. 1, 1995

[30] Foreign Application Priority Data

Jun. 17, 1994 [JP] Japan .................... 6-136051
May 9, 1995 [JP] Japan .................... 7-110415

[51] Int. Cl.$^6$ .................... C07D 207/452; A01N 43/36
[52] U.S. Cl. .................... 514/425; 548/547
[58] Field of Search .................... 548/547; 514/425

[56] References Cited

U.S. PATENT DOCUMENTS

| | | | |
|---|---|---|---|
| 3,318,766 | 5/1967 | Kato et al. | 167/33 |
| 3,428,651 | 2/1969 | Kato et al. | 260/326.3 |
| 5,310,751 | 5/1994 | Babin et al. | 514/417 |

FOREIGN PATENT DOCUMENTS

| | | |
|---|---|---|
| 0050534 | 8/1991 | European Pat. Off. . |
| 0521780 | 1/1993 | European Pat. Off. . |
| 1434956 | 6/1966 | France . |
| 2079072 | 11/1971 | France . |
| 2113124 | 11/1971 | Germany . |
| 15-23194 | 10/1940 | Japan . |
| 16-2457 | 2/1941 | Japan . |
| 57-126447 | 8/1982 | Japan . |
| 5186423 | 7/1993 | Japan . |

Primary Examiner—David B. Springer
Attorney, Agent, or Firm—Sughrue, Mion, Zinn, Macpeak & Seas

[57] ABSTRACT

Maleimide pesticides having enhanced efficacy represented by the formula (I),

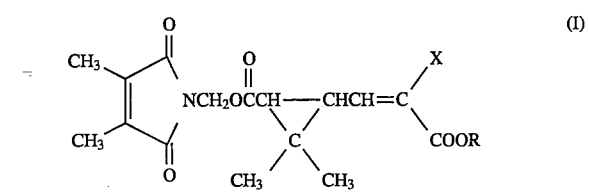

wherein X represents a halogen atom or a hydrogen atom, and R represents an alkyl group a cycloalkyl or haloalkyl group, a pesticidal composition containing the same as an active ingredient, and a process for producing the same.

10 Claims, No Drawings

MALEIMIDE PESTICIDES AND COMPOSITIONS THEREOF

BACKGROUND OF THE INVENTION

1. Field of the Invention

The present invention relates to a maleimide and a pesticidal composition containing the same as an active ingredient.

2. Related Art

Hitherto, it is described, for example, in Japanese Patent Application Kokoku No. Sho 40-23194 and Japanese Patent Application Kokai No. Hei 5-186423 that a certain kind of ester compounds is used as an active ingredient for pesticidal compositions.

However, it is not always said that those compounds are satifactory as an active ingredient for pesticidal compositions in terms of activity and the like.

SUMMARY OF THE INVENTION

In view of the situation described above, the present inventors have extensively studied to find a compound having an excellent pesticidal effect, and as a result have found that a maleimide represented by the following formula (I) has an excellent pesticidal effect. The present inventors thus completed the present invention.

The present invention provides a maleimide represented by the formula (I) (hereinafter referred to as present compound),

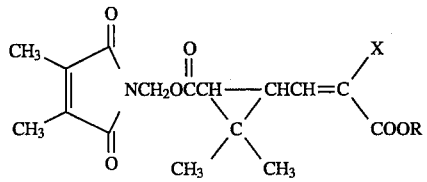

wherein X represents a halogen atom, hydrogen atom or a methyl group, and R represents an alkyl, cycloalkyl or haloalkyl group,
and a pesticidal composition containing the same as an active ingredient.

DETAILED DESCRIPTION OF THE PREFERRED EMBODIMENTS

In terms of a pesticidal effect and the like, X in the formula (I) is preferably a methyl group, hydrogen, fluorine, chlorine or bromine atom, more preferably a hydrogen or fluorine atom, and R in the formula (I) is preferably a $C_1$–$C_5$ alkyl, $C_3$–$C_5$ cycloalkyl or $C_1$–$C_5$ haloalkyl group, more preferably a $C_1$–$C_3$ alkyl (e.g. ethyl), $C_1$–$C_3$ haloalkyl (e.g. 2,2,2-trifluoroethyl or 1,1,1,3,3,3-hexafluoroisopropyl) or cyclopropyl group.

The present compound can be produced, for example, by the following method: A method of reacting a carboxylic acid compound represented by the formula (II),

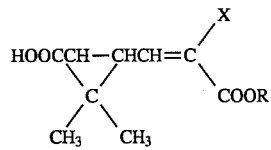

wherein X and R are as defined above, or its reactive derivative with an alcohol compound represented by the formula (III),

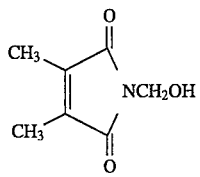

in a rate of usually 1 mole of the former to 1 to 1.5 moles of the latter.

The reactive derivative of the carboxylic acid compound represented by the formula (II) includes preferably an acid chloride compound.

The reaction of the carboxylic acid compound itself with the alcohol compound is usually carried out in an organic solvent [e.g. dichloromethane, tetrahydrofuran (THF), benzene or toluene] in the presence of a dehydrating agent [e.g. dicyclohexylcarbodiimide (DCC) or N,N-dimethylaminopropyl-N'-ethylcarbodiimide hydrochloride (WSC)]. In this reaction, an organic base such as, for example, pyridine, triethylamine, 4-dimethylaminopyridine or diisopropylethylamine may be caused to coexist. Usually, the reaction temperature is in the range of from −10° C. to +100° C. or the boiling point of the organic solvent used, preferably from 0° C. to 30° C.

The reaction of the carboxylic acid chloride with the alcohol compound is usually carried out in an organic solvent such as dichloromethane, THF, benzene or toluene in the presence of an organic base such as pyridine, triethylamine or 4-dimethylaminopyridine. The reaction temperature is in the range of from −10° C. to +100° C. or the boiling point of the organic solvent used, preferably from 0° C. to 30° C. After finish of the reaction, to the reaction solution are applied usual work-up treatments such as extraction with organic solvents, washing, concentration and the like. Thus, the desired present compound can be obtained. If necessary, the resulting compound may further be purified by usual operations such as chromatography and the like.

The present compound includes optical and geometrical isomers resulting from the cyclopropane-carboxylic acid moiety. The present invention includes all these possible optical and geometrical isomers. The preferred stereoisomer is such that the cyclopropane-carboxylic acid moiety has a (1R) configuration for the carbon atom to which the carboxyl group is bonded and the geometrical isomer of double bond of vinyl group of the moiety has an (E) form when X represents a halogen atom. When X represents a hydrogen atom or methyl group, the preferable geometrical isomer of the double bond has a (Z) form.

The carboxylic acid of the formula (II) used in the present invention can be produced, for example, according to a method described in Japanese Patent Application Kokai No. Sho 57-126447 and European Patent No. 0050534 when X is a halogen atom. When X is a hydrogen atom, the carboxylic acid of the formula II can be produced by such a method as described in Japanese Patent Application Kokai No. Sho 56-164158 and Japanese Patent Application Kokai No. Hei 1-156943.

The alcohol of the formula (III) used in the present invention is a known compound, which is described, for example, in Japanese Patent Application Kokoku No. Sho 41-2457.

The present compound exhibits a pesticidal activity, for example, against noxious life listed below. Noxious insects and mites such as:

Hemiptera:

Planthoppers (Delphacidae) such as small brown planthopper (*Laodelphax striatellus*), brown rice planthopper (*Nilaparvata lugens*), whitebacked rice planthopper (*Sogatella furcifera*), etc.; leafhoppers (Deltocephalidae) such as green rice leafhopper (*Nephotettix cincticeps*), zig-zag rice leafhopper (*Recilia dorsalis*), green rice leafhopper (*Nephotettix virescens*), etc.; aphids (Aphididae), plant bugs (Alydidae, Coreidae, Miridae, Pentatomidae, Tingidae, etc.,), whiteflies (Aleyrodidae), scale insects (Coccoidea), jumping plantlice (Psyllidae), etc.

Lepidoptera:

Pyralid moths (Pyralidae) such as rice stem borer (*Chilo suppressalis*), rice leafroller (*Cnaphalocrocis medinalis*), Indian meal moth (*Plodia interpunctella*), etc.; owlet moths (Noctuidae) such as common cutworm (*Spodoptera litura*), rice armyworm (*Pseudaletia separata*), cabbage armyworm (*Mamestra brassicae*), etc.; whites (Pieridae) such as common cabbage worm (*Pieris rapae crucivora*), etc.; bell moths (Tortricidae) such as *Adoxophyes spp.*, etc.; Carposinidae; lyonetiid moths (Lyonetiidae); tussock moths (Lymantriidae); pluslid moths (Plusiinae); *Agrotis spp.* such as turnip moth (*Agrotis segetum*), black cutworm (*Agrotis ipsilon*), etc.; *Hellothis spp.*, etc.; diamondback moth (*Plutella xylostella*), casemaking clothes moth (*Tinea translucens*), webbing clothes moth (*Tineola bisselliella*), etc.

Diptera:

House mosquitoes (*Culex spp.*) such as common mosquito (*Culex pipiens pallens*), *Culex tritaeniorhynchus*, etc.; *Aedes spp.* such as *Aedes aegypti*, *Aedes albopictus*, etc.; Anophelinae such as *Anopheles sinensis*, etc.; midges (Chironomidae); Muscidae such as houseflies (*Musca domestica*), false stableflies (*Muscina stabulans*), lesser houseflies (*Fannia canicularis*), etc.; blow flies (Calliphoridae); flesh flies (Sarcophagidae); anthomyiid flies (Anthomyiidae) such as seedcorn maggot (*Delia platura*), onion maggot (*Delia antiqua*), etc.; fruit flies (Tephritidae); small fruit flies (Drosophilidae); moth flies (Psychodidae); tabanid flies (Tabanidae); black flies (Simuliidae); stable flies (Stomoxyidae), etc.

Beetles (Coleoptera):

Corn rootworms (Diabrotica) such as western corn rootworm (*Diabrotica virgifera*), southern corn rootworm (*Diabrotica undecimpunctata*), etc.; scarabs (Scarabaeidae) such as cupreous chafer (*Anomala cuprea*), soybean beetle (*Anomala rufocuprea*), etc.; weevils (Curculionidae) such as rice water weevil (*Lissorhoptrus oryzophilus*), etc. Rhynchophoridae such as maize weevil (*Sitophilus zeamais*), etc.; darkling beetles (Tenebrionidae) such as yellow mealworm (*Tenebrio molitor*), red flour beetle (*Tribolium castaneum*), etc.; leaf beetles (Chrysomelidae) such as striped flea beetle (*Phyllotreta striolata*), cucurbit leaf beetle (*Aulacophora femoralis*), etc.; deathwatch and drugstore beetles (Anobiidae); *Epilachna spp.* such as twenty-eight-spotted ladybird (*Epilachna vigintioctopunctata*), etc.; powderpost beetles (Lyctidae); false powderpost beetles (Bostrychidae); longicorn beetles (Cerambycidae); robe beetles (*Paederus fuscipes*); etc.

Cockroaches (Dictyoptera):

German cockroach (*Blattella germanica*), smokybrown cockroach (*Periplaneta fuliginosa*), American cockroach (*Periplaneta americana*), brown cockroach (*Periplaneta brunnea*), oriental cockroach (*Blatta orientalis*), etc.

Thrips (Thysanoptera):

*Thrips palmi*, flower thrips (*Thrips hawaiiensis*, etc.;

Hymenoptera:

Ants (Formicidae), hornets (Vespidae), bethylid wasps (Bethylidae), sawflies (Tenthredinidae) such as cabbage sawfly (*Athalia rosae ruficornis*), etc.

Orthoptera:

Mole crickets (Gryllotalpidae), grasshoppers (Acrididae), etc.

Fleas (Siphonaptera):

Purex irritans, etc.

Sucking lice (Anoplura):

*Pediculus humanus, Pthirus pubis*, etc. and

Termites (Isoptera):

*Reticulitermes speratus*, Formosan subterranean termite (*Coptotermes formosanus*), etc.

Noxious mites and ticks such as:

Spider mites (Tetranychidae):

Carmine spider mite (*Tetranychus cinnabarinus*), two-spotted spider mite (*Tetranychus urticae*), Kanzawa spider mite (*Tetranychus kanzawai*), citrus red mite (*Panonychus citri*), European red mite (*Panonychus ulmi*), etc.

Ixodidae:

*Boophilus microplus*, etc., and

House dust mites:

Acaridae, Pyroglyphidae, Cheyletidae, Dermanyssidae, etc.

When the present compounds are used as an active ingredient for the pesticidal composition, it is a common practice to formulate them into the various formulations described below by mixing with a solid carrier, a liquid carrier, a gaseous carrier or a bait, or to impregnate them into base materials such as mosquito coils, mosquito mats, etc., and if necessary to add surface active agents and other auxiliaries for formulation. The above formulations include oil sprays, emulsifiable concentrates, wettable powders, flowable formulations such as, for example, water-based suspension formulations, water-based emulsion formulations, granules, dusts, aerosols, heating smoking formulations such as, for example, mosquito coils, electric mosquito mats, electric non-mat formulations, heating smoking formulations such as, for example, self-combustible smoking formulations, chemically reactive smoking formulations, porous ceramic plate-form smoking formulations, non-heating volatile formulations such as, for example, resin volatile formulations, impregnated paper voltatile formulations, foggings, ULV formulations, poisonous baits and the like.

These formulations usually contain the present compound as an active ingredient in an amount of 0.001% to 95% by weight.

The solid carrier used in formulation includes for example fine powders or granules of clays (e.g. kaolin clay, diatomaceous earth, synthetic hydrated silicon oxide, bentonire, Fubasami clay, acid clay), talcs, ceramics, other inorganic minerals (e.g. sericites, quartz, sulfur, active carbon, calcium carbonate, hydrated silica) and chemical fertilizers (e.g. ammonium sulfate, ammonium phosphate, ammonium nitrate, urea, ammonium chloride). The liquid carrier includes for example water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. hexane, cyclohexane, kerosene, gas oil), esters (e.g. ethyl acetate, butyl acetate), nitriles (e.g. acetonitrile, isobutyronitrile), ethers (e.g. diisopropyl ether, dioxane), acid amides (e.g. N,N-dimethylformamide, N,N-dimethylacetamide), halogenated hydrocarbons dichloromethane, trichloroethane, carbon tetrachloride), dimethyl sulfoxide, vegetable oils (e.g. soybean oil, cotton seed. oil), etc. The gaseous carrier, i.e. a propellant, includes for example flon gas, butane gas, LPG (liquefied petroleum gas), dimethyl ether, carbon dioxide gas and the like.

The surface active agents include for example alkyl sulfates, alkylsulfonates, alkylarylsulfonates, alkyl aryl ethers and their polyoxyethylenated products, polyethylene glycol ethers, polyhydric alcohol esters, suger alcohol derivatives and the like.

The auxiliaries for formulation such as fixing agents, dispersing agents, etc. include for example casein, gelatin, polysaccharides (e.g. starch powder, gum arabic, cellulose derivatives, alginic acid), lignin derivatives, bentonire, saccharides, synthetic water-soluble polymers (e.g. polyvinyl alcohol, polyvinyl pyrrolidone, polyacrylic acids), etc. The stabilizing agents include for example PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, surface active agents, fatty acids and their esters, and the like.

The base material for the mosquito coils includes for example mixtures of a vegetable raw powder (e.g. wood powder, pyrethrum marc) with a binder (e.g. tabu powder, starch, gluten).

The base material for the electric mosquito mats includes for example plate-like hardened products of fibrils of cotton linter or a mixture of cotton linter and pulp.

The base material for the self-combustible smoking formulations includes for example combustible exothermic agents (e.g. nitrates, nitrites, guanidine salts, potassium chlorate, nitro-cellulose, ethyl cellulose, wood powders), pyrolysis-stimulating agents (e.g. alkali metal salts, alkaline earth metal salts, dichromates, chromates), oxygen-supplying agents (e.g. potassium nitrate), combustion assistants melamine, wheat starch), fillers (e.g. diatomaceous earth) and binders (e.g. synthetic pastes).

The base material for the chemically reactive smoking formulations includes for example exothermic agents (e.g. sulfides, polysulfides, hydrosulfides and hydrate salts of alkali metals, calcium oxide), catalysts (e.g. carbonaceous substances, iron carbide, activated clay), organic foaming agents (e.g. azodicarbonamide, benzenesulfonylhydrazide, dinitrosopentamethylene-tetramine, polystyrene, polyurethane) and fillers (e.g. natural fiber pieces, synthetic fiber pieces).

The base material for the non-heating volatile formulations includes for example thermoplatic resins, filter paper and Japanese paper.

The base material for the poisonous baits include for example bait components (e.g. grain powders, vegetable oils, saccharides, crystalline cellulose), antioxidant (e.g. dibutylhydroxytoluene, nordihydroguaiaretic acid), preservatives (e.g. dehydroacetic acid), substances for preventing erroneous eating (e.g. red pepper powder), and attractants (e.g. cheese perfume, onion perfume, peanut oil).

Flowable formulations (water-based suspension or emulsion formulations) are generally obtained by finelly dispersing 1 to 75% of the present compound in water containing 0.5 to 15% of a dispersing agent, 0.1 to 10% of a suspension assistant (e.g. protective colloids, compounds giving thixotropy) and 0 to 10% of a suitable auxiliary (e.g. antifoaming agents, anticorrosives, stabilizers, spreading agents, penetration auxiliaries, antifreezing agents, antibacterial agents, antimolding agents). It is also possible to obtain oil-based suspension formulations by replacing water by an oil in which the present compound is almost insoluble. The protective colloids include for example gelatin, casein, gums, cellulose esters, polyvinyl alcohol, etc., and the compounds cjiving thioxtropy include for example bentonire, aluminum magnesium silicate, xanthane gum, polyacrylic acid and the like.

The formulations thus obtained are used as they are or diluted with water, etc. They may also be used in mixture with other insecticides, acaricides, nematicides, soil-pest controlling agents, fungicides, herbicides, plant growth regulators, synergists, fertilizers, soil improvers, etc., or may be used together with these chemicals simultaneously and without mixing.

Examples of the insecticides and acaricides used herein include for example the following:

Organophosphorus compounds such as fenitrothion [O,O-dimethyl O-(3-methyl-4-nitrophenyl)phosphorothioate), fenthion [OO-dimethyl O-(3-methyl-4-(methylthio)phenyl)-phosphorothioate), diazinon [OO-diethyl-O-2-isopropyl-6-methylpyrimidin-4-ylphosphorothioate], chlorpyriphos [OO-diethyl-O-3,5,6-trichloro-2-pyridylphosphorothioate], DDVP [2,2-dichlorovinyl dimethylphosphate], etc.;

carbamate compounds such as BPMC [2-sec-butylphenyl methylcarbamate], propoxur [2-isopropoxyphenyl N-methylcarbamate], etc.;

pyrethroid compounds such as ethofenprox [2-(4-ethoxyphenyl)-2-methylpropyl-3-phenoxybenzyl ether], fenvalerate [(RS)-α-cyano-3-phenoxybenzyl (RS)-2-(4-chlorophenyl)-3-methylbutyrate], esfenvalerate [(S)-α-cyano-3-phenoxybenzyl (S)-2-(4-chlorophenyl)-3methylbutyrate], fenpropathrin [(RS)-α-cyano-3phenoxybenzyl 2,2,3,3-tetramethylcyclopropane-carboxylate], cypermethrin [(RS)-α-cyano-3-phenoxybenzyl (1RS-cis,trans)-3-(2,2-dichlorovinyl)-2,2-dimethylcyclopropane-carboxylate], permethrin [3phenoxybenzyl (1RS-cis,trans)-3-(2,2-dichlorovinyl)-2,2dimethylcyclopropane-carboxylate], deltamethrin [(S)-α-cyano-3-phenoxybenzyl (1R-cis)-3-(2,2-dibromovinyl)-2,2-dimethylcyclopropane-carboxylate], 2-methyl-2-(4bromodifluoromethoxyphenyl)propyl (3-phenoxybenzyl) ether, tralomethrin [(1R-cis)3[(1'RS)(1',2',2',2'-tetrabromoethyl)]-2,2-dimethylcyclopropane-carboxylic acid (S)-α-cyano-3-phenoxybenzyl ester], silafluofen [4ethoxyphenyl {3-(4-fluoro-3-phenoxyphenyl)-propyl}dimethylsilane], d-phenothrin [3-phenoxybenzyl (1R-cis,trans)-chrysanthemate], cyphenothrin [(RS)-α-cyano-3-phenoxybenzyl (1R-cis,trans)-chrysanthemate], d-resmethrin [5-benzyl-3-furylmethyl (1R, cis,trans)chrysanthemate], acrinathrin [(S)-α-cyano-3-phenoxybenzyl (1R-cis(Z))-(2,2-dimethyl-3-{3-oxo-3-(1,1,1,3,3,3-hexafluoropropyloxy) propenyl}-cyclopropane-carboxylate], cyfluthrin[(RS)-α-cyano-4-fluoro-3-phenoxybenzyl 3-(2,2-dichlorovinyl)-2,2-dimethylcyclopropane-carboxylate, lambdahalothrin [(RS)-α-cyano-3-phenoxybenzyl (1RS)-cis(Z))-3-(2-chloro-3,3,3-trifluoroprop-1-enyl)-2,2-dimethylcyclopropane-carboxylate], tefluthrin [2,3,5,6-tetrafluoro-4-methylbenzyl (1RS-cis(Z))-3-(2-chloro-3,3,3-trifluoroprop-1-enyl)-2,2-dimethylcyclopropane-carboxylate], transfluthrin [2,3,5,6-tetrafluorobenzyl (1R-trans)-3-(2,2-dichlorovinyl)-2,2-dimethylcyclopropane-carboxylate], etc.; and nitroimidazolidine derivatives such as imidachloprid [1-(6-chloro-3-pyridylmethyl)-N-nitro-imidazolidin-2-ylidenamine], etc., and benzoylphenylurea compounds such as chlorofluazuron [1-(3,5-dichloro-4-(3-chloro-5-trifluoromethylpyridin-2-yloxy)phenyl)-3-(2,6-difluorobenzoyl)urea], teflubenzuron [1-(3,5-dichloro-2,4-difluorophenyl)-3-(2,6-difluorobenzoyl)urea], flufenoxuron [1-(4-(2-chloro-4-trifluoromethylphenoxy)-2-fluorophenyl)-3-(2,6-difluorobenzoyl)urea], etc.

When the present compounds are used as an active ingredient for the pesticidal compositions used in agriculture, their dosage rate is usually 0.1 to 500 g/10 ares. When the emulsifiable concentrates, wettable powders, flowable formulations, etc. are used diluted with water, the application concentration of the active ingredient is from 0.1 to 1000 ppm. The granules, dusts, etc. are used as they are without being diluted. When the present compounds are used as an active ingredient for the pesticidal compositions used for household and public hygiene, the emulsifiable concentrates, wettable powders, flowable formulations, etc. are applied diluted with water 0.1 to 10000 ppm, and the oil sprays, aerosols, fumigants, smoking formulations, volatile formulations, foggings, ULV formulations, poisonous baits, etc. are applied as they are.

Any of these dosage rate and application concentration varies with the kind of formulations, when, where and how these formulations are applied, the kind of pests, the degree of damage, etc., and therefore they may be increased or decreased independently of the ranges described above.

The present invention will be illustrated in more detail with reference to the following preparation examples, formulation examples and test examples, but it is not limited to these examples.

PREPARATION EXAMPLE 1

Three hundred milligrams of (1R, cis)-2,2-dimethyl-3(E)-[2-fluoro-2-(ethoxycarbonyl)ethenyl]-cyclopropane-1-carboxylic acid and 243 mg of N-(hydroxymethyl)dimethylmaleimide were dissolved in 4 ml of dry dichloromethane. To the resulting solution were added at room temperature 275 mg of N,N-dimethylaminopropyl-N'-ethylcarbodiimide hydrochloride (WSC), 200 µl of triethylamine and a catalytic amount of 4-dimethylaminopyridine. After stirring was continued for 12 hours at the same temperature, the reaction solution was poured into a cold aqueous dilute solution of citric acid, and extracted three times with dichloromethane. The dichloromethane layers were combined, washed with a saturated aqueous sodium chloride solution and dried over anhydrous magnesium sulfate. The solvent was then distilled off under reduced pressure. The residue was subjected to column chromatography on silica gel [eluent, n-hexane:ethyl acetate=3:1 (V/V)] to obtain 205 mg of the desired dimethylmaleimidomethyl (1R, cis)-2,2-dimethyl-3(E)-[2-fluoro-2-(ethoxycarbonyl) ethenyl]-cyclopropane-1-carboxylate [present compound (1)] as a colorless, transparent, viscous oily product (yield, 43%).

$n^{20}_D$ 1.5040 $[\alpha]^{22}_D$ +3.8° (c=0.37, CHCl$_3$) $^1$H-NMR (solvent, CDCl$_3$; internal standard, TMS) δ value (ppm): 6.37 (dd, 1H), 5.50 (S, 2H), 4.30 (q, 2H), 2.86 (br, t, 1H), 2.01 (s, 6H), 1.83 (d, 1H), 1.35 (t, 3H), 1.26 (s, 3H), 1.24 (s, 3H) $^{19}$F-NMR (solvent, CDCl$_3$; internal standard, CCl$_3$F) δ value (ppm): −120.44 (d, 1F)

PREPARATION EXAMPLE 2

Seven hundred and sixty-nine milligrams of (1R, cis)-2,2-dimethyl-3-(E)-[2-fluoro-2-(ethoxYcarbonyl)ethenyl]-cyclopropane-1-carboxylic acid was dissolved in 5 ml of dry benzene. After adding 350 µl of oxalyl chloride, reaction was carried out for 1 hour under reflux with heating. The reaction solution was concentrated under reduced pressure to obtain the corresponding carboxylic acid chloride.

Separately, 570 mg of N-(hydroxymethyl)dimethylmaleimide, 400 mg of pyridine and a catalytic amount of 4-dimethylaminopyridine were dissolved in 5 ml of dry benzene. To the resulting solution was added dropwise the benzene solution (5 ml) of the above prepared carboxylic acid chloride under ice-cooling, after which stirring was continued at room temperature for 14 hours. The reaction solution was poured into an ice-cooled aqueous dilute solution of citric acid, and extracted three times with diethyl ether. The organic layers were combined, washed with saturated aqueous sodium chloride solution and dried over anhydrous magnesium sulfate. The solvent was then distilled off under reduced pressure. The residue was subjected to column chromatography on silica gel [eluent, n-hexane:ethyl acetate=3:1 (V/V)] to obtain 770 mg of the desired dimethylmaleimidomethyl (1R, cis)-2,2-dimethyl-3-(E)-[2-fluoro-2-(ethoxycarbonyl) ethenyl]cyclopropane-1carboxylate [present compound (1)] as a colorless, transparent, viscous oily product (yield, 63%).

The physical properties of the resulting compound showed the same values as those of the compound obtained in Preparation Example 1 within a range of a bias in measurement.

PREPARATION EXAMPLE 3

One hundred sixty one milligrams of N-(hydroxymethyl)dimethylmaleimide and 0.25 ml of triethylamine and a catalytic amount of 4-dimethylaminopyridine were dissolved in 5.0 ml of dry tetrahydrofuran and the resultant solution was cooled to 0° C. To thus prepared solution was added dropwise 2.0 ml of tetrahydrofuran solution containing 210 mg of (1R, cis) 2,2-dimethyl-3-(Z)-[2-(ethoxycarboxyl)ethenyl]-cyclopropane-1-carboxylic acid chloride, and the resultant solution was stirred for 14 hours at room temperature. The reaction solution was poured into a saturated ammonium chloride aqueous solution, and extracted three times with diethyl ether. The diethyl ether layers was combined, wished with a saturated aqueous sodium chloride solution and dried over anhydrous magnesium sulfate. The solvent was then distilled off under reduced pressure. The residue was subjected to column chromatography on silica gel [eluent, n-hexane:ethyl acetate=4:1 (V/V)] to obtain 269 mg of the desired dimethylmaleimidomethyl (1R,cis)-2,2-dimethyl-3(Z)-[2-ethoxycarbonyl)-ethenyl]cyclopropane-1carboxylate [present compound (4)] (yield, 85%).

n 1.5049 $^1$H-NMR (solvent, CDCl$_3$; internal standard, TMS) δ value (ppm): 6.58 (br, t, 1H), 5.89 (d, 1H), 5.52 (d, 1H), 5.47 (d, 1H), 4.17 (q, 2H), 3.65 (br, t, 1H), 2.01 (s, 6H), 1.87 (d, 1H), 1.30 (t, 3H), 1.30 (s, 3H), 1.25 (s, 3H)

PREPARATION EXAMPLE 4

To a mixture solution of 3 ml of dry tetrahydrofuran and 951 µl of dry pyridine was added dropwise 17.2 µl of thionyl chloride at −10° C. To the resultant solution was added dropwise 2 ml of dry tetrahydrofuran solution containing 500 mg of (1R,trans)-2,2-dimethyl-3-(E)-[2-(methoxycarbonyl)-1-propenyl]-cyclopropane-1-carboxylic acid at −10° C. The resultant solution was stirred for 15 minutes at the same temperature. Thereafter, 2 ml of dry tetrahydrofuran containing 366 mg of N-(hydroxmethyl)dimethylmaleimide was added to said solution and the resultant solution was continued to stir for 12 hours at room temperature.

The reaction solution was poured into an ice-cooled aqueous dilute solution of citric acid, and extracted three times with diethyl ether. The diethyl ether layers were combined, washed with saturated aqueous sodium chloride solution, and dried over anhydrous magnesium sulfate. The solvent was then distilled off under reduce pressure. The residue was subjected to column chromatography on silica gel [eluent, n-hexane:ethyl acetate=3:1] to obtain 460 mg of the desired dimethylmaleimidomethyl (1R, trans)-2,2-dimethyl-3-(E)-[2-(methoxycarbonyl)-1-propenyl]cyclopropane-1carboxylate [present compound (6)] as a crystalline product (yield, 56%).

Melting point: 98.7° C. (uncorrected) $^1$H-NMR (solvent, CDCl$_3$; internal standard, TMS) δ value (ppm): 6.41 (m, 1H), 5.53 (ABq, 2H), 3.72 (s, 3H), 2.20 (q, 1H), 2.01 (s, 6H), 1.92 (br, s, 3H), 1.66 (d, 1H), 1.31 (s, 3H), 1.21 (s, 3H)

Examples of the present compound will be shown below together with their compound numbers.

(1) Dimethylmaleimidomethyl (1R,cis)-2,2-dimethyl-3(E)-[2-fluoro-2-(ethoxycarbonyl) ethenyl]cyclopropane-1carboxylate (2) Dimethylmaleimidomethyl (1R, cis)-2,2-dimethyl-3(E)-[2-fluoro-2-(cyclopropyloxycarbonyl) ethenyl]-cyclopropane-1-carboxylate (3) Dimethylmaleimidomethyl (1R,cis)-2,2-dimethyl-3(E)-[2-fluoro-2-(2,2,2-trifluoroethoxycarbonyl) ethenyl]-cyclopropane-1-carboxylate (4) Dimethylmaleimidomethyl (1R, cis)-2,2-dimethyl-3(Z)-[2-(ethoxycarbonyl) ethenyl]cyclopropane-1carboxylate (5) Dimethylmaleimidomethyl (1R,cis)-2,2-dimethyl-3(Z)-[2-(1,1,1,3,3,3-hexafluoroisopropyloxycarbonyl) ethenyl] cyclopropane-1-carboxylate (6) Dimethylmaleimidomethyl (1R, tran)-2,2-dimethyl-3(E)-[2-(methoxycarbonyl) propenyl]cyclopropanecarboxylate Formulation examples will be shown below. In the examples, part is by weight, and the present compounds will be shown by the compound numbers shown above.

FORMULATION EXAMPLE 1 EMULSIFIABLE CONCENTRATE

Twenty parts of each of the compounds (1) to (6) is dissolved in 65 parts of xylene, and 15 parts of Sorpol 3005X, an emulsifier (a registered trade mark of Toho Kagaku Co., Ltd.) is added thereto. The resulting mixture is well stirred and mixed to obtain a 20% emulsifiable concentrate of each compound.

FORMULATION EXAMPLE 2 WETTABLE POWDER

To 40 parts of each of the compounds (1) to (6) is added 5 parts of Sorpol 3005X (described above), and after well stirring, 32 parts of Carplex #80, finely powdered synthetic hydrated silicon oxide (a registered trade mark of Shionogi Seiyaku Co., Ltd.) and 23 parts of 300-mesh diatomaceous earth are added thereto. The resulting mixture is well stirred and mixed with a juice mixer to obtain a 40% wettable powder of each compound.

FORMULATION EXAMPLE 3 GRANULE 1.5 Parts of each of the compounds (1) to (6) and 98.5 parts of AGSORB LVM-MS24/48, a calcined product of montmorillonite (a granular carrier of 24 to 48 mesh in particle size; produced by OIL DRI Co., Ltd.), are well mixed to obtain a 1.5% granule of each compound.

FORMULATION EXAMPLE 4 MICROENCAPSULATED FORMULATION

Ten parts of each of the compounds (1) to (6), 10 parts of phenylxylylethane and 0.5 part of Sumidur L-75, tolylenediisocyanate (produced by Sumitomo Bayer Urethane Co., Ltd.) are mixed. The resulting mixture is added to 20 parts of a 10% aqueous gum arabic solution and stirred with a homomixer to obtain an emulsion of 20 μm in average particle size. Thereafter, 2 parts of ethylene glycol is added thereto and reaction is carried out for 24 hours at 60° C. in a warm bath to obtain a microcapsule slurry.

Separately, 0.2 part of xanthane gum and 1.0 part of Veegum R, aluminum magnesium silicate (produced by Sanyo Kasei Co., Ltd.), are dispersed in 56.3 parts of ion-exchanged water to obtain a thickening agent solution.

42.5 Parts of the above microcapsule slurry and 57.5 parts of the above thickening agent solution are mixed to obtain a 10% microencapsulated formulation of each compound.

FORMULATION EXAMPLE 5 FLOWABLE FORMULATION

Ten parts of each of the compounds (1) to (6) and 10 parts of phenylxylylethane are mixed, added to 20 parts of a 10% aqueous polyethylene glycol solution and stirred with a homomixer to obtain an emulsion of 3 μm in average particle size.

Separately, 0.2 part of xanthane gum and 1.0 part of Veegum R, aluminum magnesium silicate (produced by Sanyo Kasei Co., Ltd.), are dispersed in 58.8 parts of ion-exchanged water to obtain a thickening agent solution.

Forty parts of the above emulsion and 60 parts of the above thickening agent solution are mixed to obtain a 10% flowable formulation of each compound.

FORMULATION EXAMPLE 6 DUST

Five parts of each of the compounds (1) to (6), 3 parts of Carplex #80 (described above), 0.3 part of PAP and 91.7 parts of 300-mesh talc are mixed with stirring with a juice mixer to obtain a 5% dust of each compound.

FORMULATION EXAMPLE 7 OIL SOLUTION 0.1 Part of each of the compounds (1) to (6) is dissolved in 5 parts of dichloromethane, and mixed with 94.9 parts of deodorized kerosene to obtain a 0.1% oil solution of each compound.

FORMULATION EXAMPLE 8 OIL-BASED AEROSOL

One part of each of the compounds (1) to (6), 5 parts of dichloromethane and 34 parts of a deodorized kerosene are mixed into a solution. The resulting solution is put in an aerosol container. After attaching a valve part to the container, 60 parts of a propellant (liquefied petroleum gas) is charged into the container under pressure through the valve part to obtain an oil based aerosol of each compound.

FORMULATION EXAMPLE 9 WATER-BASED AEROSOL 0.6 Part of each of the compounds (1) to (6), 5 parts of xylene, 3.4 parts of a deodorized kerosene and 1 part of an emulsifier, Atoms 300 (a registered trade mark of Atlas Chemical Co., Ltd.) are mixed into a solution. The resulting solution and 50 parts of pure water are put in an aerosol container. After attaching a valve part to the container, 40 parts of a propellant (liquefied petroleum gas) is charged into the container under pressure through the valve part to obtain a water-based aerosol of each compound.

FORMULATION EXAMPLE 10 MOSQUITO COIL 0.3 Gram of each of the compounds (1) to (6) is dissolved in 20 ml of acetone and uniformly mixed with 99.7 g of a mosquito coil carrier (a mixture of tabu powder, pyrethrum marc and wood powder in a weight ratio of 4:3:3) with stirring. After adding 120 ml of water to the resulting mixture, the mixture is well kneaded, shaped into a mosquito coil and dried to obtain a mosquito coil of each compound.

FORMULATION EXAMPLE 11 ELECTRIC MOSQUITO MAT FORMULATION 0.8 Gram of each of the compounds (1) to (6) and 0.4 g of piperonyl butoxide are dissolved in acetone, and the total volume of the solution is made up to 10 ml with acetone. Thereafter, 0.5 ml of this solution is uniformly impregnated into a base material for electric mats of 2.5 cm×1.5 cm×0.3 cm (thickness) (a plate-like hardened product of fibrils of a mixture of cotton linter and pulp) to obtain an electric mosquito mat formulation of each compound.

FORMULATION EXAMPLE 12 ELECTRIC MOSQUITO LIQUID FORMULATION

Three parts of each of the compounds (1) to (6) is dissolved in 97 parts of a deodorized kerosene and put in a vinyl chloride container. A liquid-absorbing core (a sintered product of an inorganic powder hardend with a binder), of which the upper part is made so that it can be heated with a heater, is inserted into the container to obtain an electric mosquito liquid formulation of each compound.

FORMULATION EXAMPLE 13 HEATING SMOKING FORMULATION

One hundred milligrams of each of the compounds (1) to (6) is dissolved in a suitable amount of acetone, and impregnated into a porous ceramic plate of 4.0 cm×4.0 cm×1.2 cm (thickness) to obtain a heating smoking formulation of each compound.

FORMULATION EXAMPLE 14 ROOM-TEMPERATURE VOLATILE FORMULATION

One hundred μg of each of the compounds (1) to (6) is dissolved in a suitable amount of acetone, and uniformly coated onto a filter paper of 2 cm×2 cm×0.3 mm (thickness). Acetone is removed by air-drying to obtain a room-temperature volatile formulation of each compound.

FORMULATION EXAMPLE 15 MITE-CONTROLLING SHEET

An acetone solution of each of the compounds (1) to (6) is dropped to a filter paper and impregnated into the paper so that the amount of the compound is 1 per $m^2$. Acetone is removed by air-drying to obtain a mite-controlling sheet of each compound.

Test examples will be shown for the purpose of showing that the present compound is useful as an active ingredient for pesticidal compositions. The present compounds are shown by the foregoing compound numbers, and compounds used as a control are shown by compound symbols described in Table 1.

TABLE 1

| Compound symbol | Chemical structure | Remark |
|---|---|---|
| (A) | [structure: cyclohexene dicarboximide with N-CH₂OC(O)CH—CHCH=C(F)(COOC₂H₅), with C(CH₃)(CH₃) cyclopropane; (1R-cis, E)] | Compound described in Example 1 of Japanese Patent Application Kokai No. Hei 5-186423. |
| (B) | [structure: dimethylmaleimide with N-CH₂OC(O)CH—CHCH=C(CH₃)(CH₃), with C(CH₃)(CH₃) cyclopropane; (1R-trans)] | Optical isomer of a compound described in Japanese Patent Application Kokoku No. Sho 40-23194. |

TEXT EXAMPLE 1

Six adults (three males and three females) of smokybrown cockroach (*Periplaneta fuliginosa*) were liberated in a container of which the inner wall surface was thinly coated with margarine and the bottom was made of a wire net. The container was then set in a CSMA chamber. Thereafter, 1.5 ml of the 0.1% oil solution of each test compound obtained according to Formulation Example 7 was directly sprayed from the top of the chamber under a pressure of 0.42 atm. by means of a spray gun. After 1 minute, the number of the knocked-down insects was examined. The results are shown in Table 2.

TABLE 2

| Compound | Percent knock-down (%) |
|---|---|
| (1) | 100 |
| (2) | 100 |
| (A) | 33 |

TEXT EXAMPLE 2

Ten adults (five males and five females) of German cockroach (*Blattella germanica*) were liberated in a polyethylene cup of 9 cm in diameter which was thinly coated with margarine at the inner wall surface. The cup was closed with a 16-mesh nylon gauze, and placed at the bottom of an acrylic cylinder of 10 cm in inside diameter and 37 cm in height. Thereafter, 0.6 ml of the 0.1% oil solution of each test compound obtained according to Formulation Example 7 was directly sprayed from the top of the cylinder under a pressure of 0.6 atm. by means of a spray gun. After 1 minute, the number of the knocked-down insects was examined. The results are shown in Table 3.

TABLE 3

| Compound | Percent knock-down (%) |
|---|---|
| (1) | 100 |
| (2) | 100 |
| (3) | 100 |
| (4) | 100 |
| (5) | 100 |
| (B) | 30 |

TEXT EXAMPLE 3

Ten female adults of common mosquito (*Culex piplens pallens*) were liberated in a 70 cm-cube (0.34 m$^3$) ass chamber. Thereafter, 0.7 ml of the 0.1% oil solution of each test compound obtained according to Formulation Example 7 was sprayed into the chamber under pressure of 0.8 atm. by means of a spray gun. After 0.6 minute, the number of the knocked-down insects was examined. The results are shown in Table 4.

TABLE 4

| Compound | Percent knock-down (%) |
|---|---|
| (1) | 90 |
| (6) | 70 |
| (B) | 0 |

TEXT EXAMPLE 4

Ten adults (five males and five females) of housefly (*Musca domestica*) were liberated in a 70 cm-cube (0.34 m$^3$) glass chamber. Thereafter, 0.7 ml of the 0.00625% oil solution of each test compound obtained according to Formulation Example 7 was sprayed into the chamber under a pressure of 0.8 atm. by means of a spray gun. After 3.5 minutes, the number of the knocked-down insects was examined. The results are shown in Table 5.

TABLE 5

| Compound | Percent knock-down (%) |
|---|---|
| (1) | 100 |
| (2) | 100 |
| (B) | 21 |

The present compounds show an excellent pesticidal effect.

What is claimed is:

1. A maleimide represented by the formula (I),

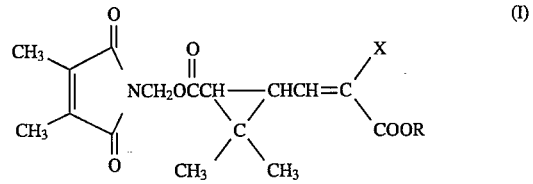

wherein X represents a halogen atom or a hydrogen atom, and R represents an alkyl, cycloalkyl or haloalkyl group.

2. A maleimide according to claim 1, wherein X is a hydrogen, fluorine, chlorine, or bromine atom, and R is a $C_1$–$C_5$ alkyl, $C_3$–$C_5$ cycloalkyl or $C_1$–$C_5$ haloalkyl group.

3. A maleimide according to claim 1, wherein X is a hydrogen or fluorine atom, and R is a $C_1$–$C_3$ alkyl, cyclopropyl or $C_1$–$C_3$ haloalkyl group.

4. Dimethylmaleimidomethyl (1R, cis)-2,2-dimethyl-3(E)-[2-fluoro-2-(ethoxycarbonyl) ethenyl]cyclopropane-1-carboxylate.

5. Dimethylmaleimidomethyl (1R, cis)-2,2-dimethyl-3(E)-[2-fluoro-2-(cyclopropyloxycarbonyl) ethenyl]cyclopropane-1-carboxylate.

6. Dimethylmaleimidomethyl (1R, cis)-2,2-dimethyl-3(E)-[2-fluoro-2-(2,2,2-trifluoroethoxycarbonyl) ethenyl]-cyclopropane-1-carboxylate.

7. Dimethylmaleimidomethyl (1R,cis)-2,2-dimethyl-3(Z)-[2-(ethoxycarbonyl) ethenyl]cyclopropane-1carboxylate.

8. Dimethylmaleimidomethyl (1R,cis)-2,2-dimethyl-3(Z)-[2-(1,1,1,3,3,3-hexafluoroisopropyloxycarbonyl) ethenyl]cyclopropane-1-carboxylate.

9. A pesticidal composition comprising as an active ingredient a maleimide represented by the formula (I),

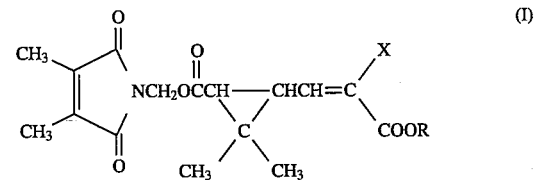

wherein X represents a halogen atom or a hydrogen atom, and R represents an alkyl, cycloalkyl or haloalkyl group, and an inert carrier.

10. A method for controlling noxious insect pests, which comprises applying an effective amount of the maleimide of claim 1, or a mixture thereof, to a locus where said insect pests propagate.

* * * * *